(12) United States Patent
Sorrell et al.

(10) Patent No.: US 9,234,159 B2
(45) Date of Patent: Jan. 12, 2016

(54) METHODS OF PREPARING HYDROXY FUNCTIONAL ANIMAL FATS

(71) Applicant: BioBased Technologies LLC, Springdale, AR (US)

(72) Inventors: Amy Sorrell, Fayetteville, AR (US); Trevor Newbold, Salt Spring (CA); Jianghong Qian, Fayetteville, AR (US); Srikanth Yalamanchili, Bentonville, AR (US); Neil Nodelman, Fayetteville, AR (US)

(73) Assignee: BIOBASED TECHNOLOGIES LLC, Rogers, AR (US)

( * ) Notice: Subject to any disclaimer, the term of this patent is extended or adjusted under 35 U.S.C. 154(b) by 289 days.

(21) Appl. No.: 13/797,692

(22) Filed: Mar. 12, 2013

(65) Prior Publication Data

US 2013/0217798 A1    Aug. 22, 2013

Related U.S. Application Data

(63) Continuation-in-part of application No. 13/066,096, filed on Apr. 6, 2011, now Pat. No. 8,674,124.

(60) Provisional application No. 61/341,926, filed on Apr. 7, 2010.

(51) Int. Cl.
*C07C 51/16* (2006.01)
*C11C 3/00* (2006.01)
*C07D 303/14* (2006.01)

(52) U.S. Cl.
CPC .............. *C11C 3/006* (2013.01); *C07D 303/14* (2013.01)

(58) Field of Classification Search
CPC ........................................................ C07C 51/16
USPC .......................................................... 554/138
See application file for complete search history.

(56) References Cited

U.S. PATENT DOCUMENTS

| 1,926,769 | A | 9/1933 | Hailwood et al. |
|---|---|---|---|
| 2,073,011 | A | 3/1937 | Hubbuch |
| 2,485,160 | A | 10/1949 | Niederhauser et al. |
| 2,752,376 | A | 6/1956 | Julian et al. |
| 3,169,139 | A | 2/1965 | D'Addieco |
| 4,749,517 | A | 6/1988 | Chwang et al. |
| 7,279,448 | B2 | 10/2007 | Erhan et al. |
| 7,560,578 | B2 | 7/2009 | Ahmad et al. |
| 7,893,287 | B2 * | 2/2011 | Casper et al. ................ 554/138 |
| 8,308,975 | B2 | 11/2012 | Roh et al. |

(Continued)

FOREIGN PATENT DOCUMENTS

| DE | 4332292 | 3/1995 |
|---|---|---|
| WO | WO-2006-014521 | 2/2006 |

OTHER PUBLICATIONS

Friguelli et al. "One-Pot-Two Steps Synthesis of 1,2-Diol." *Synthetic Communications*, 1989, 19(11 & 12):1939-1943.

(Continued)

*Primary Examiner* — Deborah D Carr
(74) *Attorney, Agent, or Firm* — Wilson Sonsini Goodrich & Rosati

(57) ABSTRACT

Simple, economical preparative processes for the provision of pure hydroxyl functional materials derived by converting unsaturated molecules found in animal fats into hydroxyl groups are presented herein. The hydroxylated animal fats can be reacted with isocyanates to form polyurethane articles.

22 Claims, 6 Drawing Sheets

(56) References Cited

U.S. PATENT DOCUMENTS

| | | |
|---|---|---|
| 8,350,070 B2 | 1/2013 | Casper et al. |
| 8,399,693 B2 | 3/2013 | Yalamanchili et al. |
| 8,507,701 B2 * | 8/2013 | Yalamanchili et al. ....... 554/138 |
| 8,674,124 B2 | 3/2014 | Newbold et al. |
| 2006/0041156 A1 | 2/2006 | Caspar et al. |
| 2006/0041157 A1 | 2/2006 | Petrovic et al. |
| 2011/0251411 A1 | 10/2011 | Newbold et al. |
| 2011/0313124 A1 | 12/2011 | Yalamanchili et al. |
| 2012/0172610 A1 | 7/2012 | Casper et al. |
| 2012/0178949 A1 | 7/2012 | Yalamanchili et al. |

OTHER PUBLICATIONS

Luong et al. "Direct Hydroxylation of Fats and Derivatives with a Hydrogen Peroxide Tungstic Acid System" *Journal of American Oil Chemists' Society*, 1967, 44:316-320.

Putilov et al. Chem. Abstr., 2003, 140-202144.

U.S. Appl. No. 14/188,506 Office Action dated Mar. 25, 2015.

\* cited by examiner

1)

2)

3)

4)

Epoxide Content %

Reaction Time (hrs)

(1) y= -0.0003x² - 0.00001x + 0.0256
    R² = 0.9574
(2) y= -0.0003x² + 0.0055x +0.0105
    R² = 0.9671

(A) = 25% H₂O₂
(B) = 70% H₂O₂

METHODS OF PREPARING HYDROXY FUNCTIONAL ANIMAL FATS

CROSS-REFERENCE

This application is a continuation-in-part application of Ser. No. 13/066,096, filed Apr. 6, 2011, which claims the benefit of U.S. Provisional Application No. 61/341,926, filed Apr. 7, 2010, both of which are incorporated herein by reference.

BACKGROUND OF THE INVENTION

Polyols are preferred compounds in polymer chemistry, due to their multiple hydroxyl functional groups available for organic reactions. Polymeric polyols react with isocyanates to form polyurethanes. Additionally, some polyols may be classified as polyether polyols, which are made by reacting epoxides with an active hydrogen containing starter compounds. These may also react with isocyanates to form polyurethanes. Polyurethanes have a number of commercial applications, including foams, potting compounds, cast resins, coatings, elastomers, adhesives, sealants, non-reinforced and fiber reinforced plastics processed using resin transfer molding (RTM), and reaction injection molding (RIM), filament winding, and pultrusion techniques.

Soybean oil can be converted to hydroxy functional soybean oil. The addition of hydroxy functionality is typically accomplished by adding hydroxyl groups (—OH) to the carbons. These polyols are then used as reactants to make polymers. The hydroxyl functional groups in polyols can be reacted with isocyanates to make polyurethanes.

SUMMARY OF THE INVENTION

In one aspect, described herein is a process of preparing a hydroxyl functional animal fat, the process comprising: providing a reactor; adding raw animal fat and an organic acid or peracid to the reactor to form an organic phase and an aqueous phase; heating the organic phase and the aqueous phase to about 50-135° C. with agitation generating a hot mixture; metering 25-70% weight/weight hydrogen peroxide/water to the hot mixture, generating a reaction mixture; heating the reaction mixture in a range of 50-135° C. for about 1 to 168 hours; stripping off the bulk of the organic acid, water, and other low boilers at or below 170° C. and at a negative pressure less than 60 mm Hg until the reaction mixture tests for an acid number less than 10 mg KOH/g, creating the hydroxyl functional animal fat.

In another aspect, described herein is a process of preparing a hydroxyl functional animal fat, the process comprising: providing a reactor; adding raw animal fat and an organic acid or peracid to the reactor to form an organic phase and an aqueous phase; heating the organic phase and the aqueous phase to about 50-135° C. with agitation generating a hot mixture; metering 35-70% weight/weight hydrogen peroxide/water to the hot mixture, generating a reaction mixture; heating the reaction mixture in a range of 50-135° C. for about 1 to 24 hours; stripping off the bulk of the organic acid, water, and other low boilers at or below 170° C. and at a negative pressure that does not exceed 60 mm Hg; heating the hydroxyl functional animal fat to about 170-270° C. under vacuum, until the hydroxyl functional animal fat tests for an acid number of about 6 mg KOH/g or less, preferably 4 mg KOH/g or less, more preferably 2 mg KOH/g or less, or most preferably 1 mg KOH/g or less.

In a further aspect, described herein is a process of preparing a hydroxy functional animal fat, the process comprising adding raw animal fat and optionally a vegetable oil, to an organic acid or peracid in a reactor to form mixture; heating the mixture to about 50-150° C. with agitation generating a hot mixture; adding 25 to 70% w/w of hydrogen peroxide/water to the hot mixture of (B) generating a reaction mixture; heating the reaction mixture in a range of 50-150° C. for about 1 to 168 hours; stripping off the bulk of the organic acid, water and other low boilers at or below a stripping temperature of 170° C. at a negative pressure that does not exceed 60 mmHg, until the reaction mixture tests for an acid number of about 10 mg KOH/g or less, creating the hydroxyl functional animal fat. In certain embodiments, the stripping comprises wiped film evaporation, short path distillation, packed column stripping, or a combination thereof. In some embodiments, the process further comprises sparging the reaction mixture with a non-reactive gas during the stripping step. In some embodiments, the non-reactive gas is steam or nitrogen. In certain embodiments, the organic acid is selected from formic acid, acetic acid, performic acid, and peracetic acid. In some embodiments, the animal fat is chicken fat, beef tallow, or lard. In specific embodiments, the animal fat is chicken fat. In some embodiments, the optional vegetable oil is soybean oil. In certain embodiments, the reaction mixture tests for an acid number of about 4 mg KOH/g or less. In some embodiments, the process further comprises heating the hydroxy functional animal fat under vacuum to about 170-270° C. until the hydroxyl functional animal fat tests for an acid number of about 2 mg KOH/g or less.

In another aspect, described herein is a hydroxy functional animal fat having an acid number of about 6 mg KOH/g or less, and 0.1% w/w or less of water. In a further aspect, described herein is a hydroxy functional animal fat derived from one or more raw animal fat and one or more vegetable oils, having an acid number of about 6 mg KOH/g or less, and 0.1% w/w or less of water.

In one aspect described herein is a polyol comprising a reaction product of an epoxidized animal fat; and a nucleophile. In some embodiments, the nucleophile is selected from water, an alcohol, a primary or secondary amine, and an organic acid. In certain embodiments, the reaction product is formed in the presence of a catalyst. In some embodiments, the epoxidized animal fat is prepared from chicken fat, beef tallow, or lard. In certain embodiments, the epoxidized animal fat is prepared from chicken fat. In some embodiments, the polyol further comprises a vegetable oil derived polyol.

In another aspect described herein is a polyol comprising a reaction product of an animal fat; hydrogen peroxide; and an organic acid. In certain embodiments, the animal fat is chicken fat, beef tallow, lard, or a combination thereof. In some embodiments, the animal fat is chicken fat. In certain embodiments, the polyol further comprises a vegetable oil derived polyol.

Also described herein is a process of preparing a hydroxy functional animal fat having an acid number of about 10 mg KOH/g or less, the process comprising contacting a raw animal fat and optionally a vegetable oil with hydrogen peroxide and an organic acid in the presence of water for a sufficient period of time, a sufficient temperature, and a sufficient pressure to form hydroxyl groups from unsaturated moieties in the raw animal fat, and thereafter separating any volatiles from the hydroxy functional animal fat by distillation, wherein the organic acid comprises formic acid, acetic acid, or propionic acid. In some embodiments, the time of reaction is from 1 to 24 hours. In certain embodiments, the temperature ranges from about 50-135° C. In some embodiments, the organic acid is a mixture of two organic acids. In certain embodiments, the distillation is carried out at or below 150° C. In some embodiments, the distillation is wiped film evaporation, short path distillation, packed column stripping, or a combination of thereof. In certain embodiments, the hydroxy functional animal fat has an acid number of about 2 mg KOH/g or less. In some embodiments, the distillation is carried out at a temperature of between about 175° C. and about 260° C.

Further described herein is the use of the hydroxy functional animal fat or polyols described herein in the preparation of polyurethanes. In certain embodiments, a polyurethane foam or slabstock foam is prepared from a hydroxy functional animal fat or polyol described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
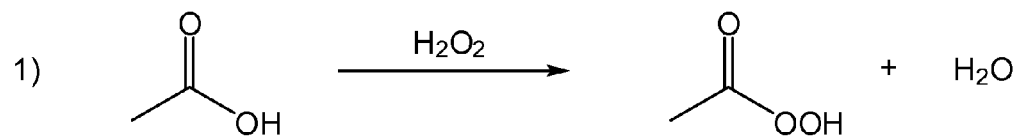
FIG. 1 is a schematic of the proposed reaction scheme to prepare the products of process.
Figure 1:
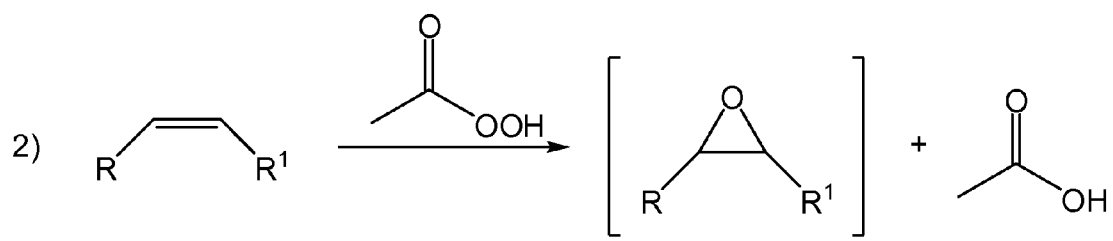
Figure 1:
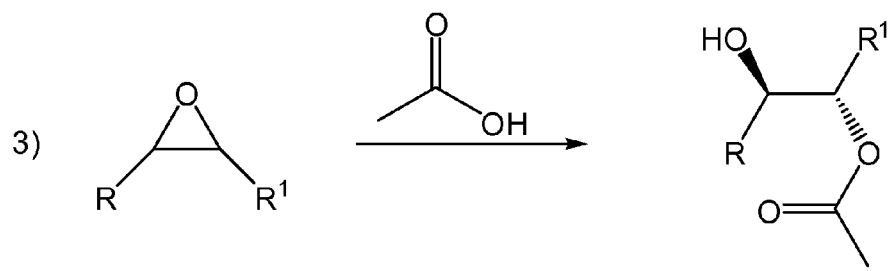
Figure 1:
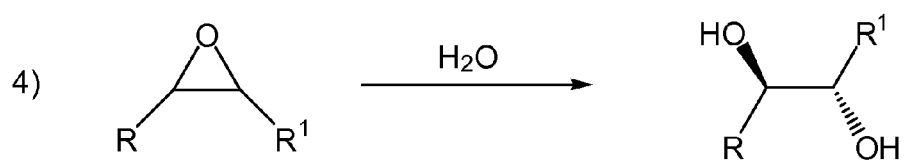

Animal fats, including chicken fat, have not been used as raw materials for producing polyols that are useful in producing polyurethane and polyurethane foams although chicken fat, for instance, is abundantly available and accounts for about 30% by weight of the total meat of the chicken.

Soybean oil derived polyols are readily available in the U.S. marketplace. A major portion of the total volume of these soybean oil polyols has found its way into the flexible slabstock foam market for seating and bedding applications. Even at low replacement levels of the petroleum-based polyether polyols, the soy-based polyols impart a "soy-like" odor to the polyurethane foam, which although very mild, is objectionable to mattress manufacturers. The polyol odor is acquired during the manufacturing of the polyol since the refined soybean oil is practically odorless. As a result, the polyols must undergo an additional purification step like wiped-film evaporation.

In contrast to soybean oil, chicken fat is a highly odorous raw material which would be expected to produce an even higher level of odor when subjected to the hydroxylation process to form a natural polyol. Surprisingly it has been found that chicken fat derived polyols, produced without undergoing a wiped film evaporation procedure, and especially the flexible foams prepared using them, have very low odor as determined by persons comprising an odor panel. It was also surprising to find that these polyols are produced as liquids at room temperature, despite the fact that the saturation content of chicken fat is double that of soybean oil.

The hand-mix slabstock foams prepared from a chicken fat derived polyol at a 15% replacement level of the polyether polyol had physical properties very similar to foams made from commercially available soybean oil derived polyols at the same polyether polyol replacement level. Based on these results, it is concluded that animal fats, like chicken fat, can be used as a very economical natural raw material for producing polyols for use in polyurethane foams.

In certain embodiments, the animal fat derived polyols should not have commercially detrimental aesthetic qualities. For example, many known vegetable based polyols have an unpleasant odor that is carried over into polymer products. Described herein are animal fat derived polyols that are characterized by an acceptable odor.

In addition, animal fat based polyols should possess a low acid number (a measure of the remaining fatty acid in the polyols) to function well in urethane systems. Polyols with elevated acid numbers tend to produce sub-optimal polyurethanes because the remaining acids can interfere with catalysts utilized in polymerization reactions and/or participate in unwanted side reactions. Utilizing separate neutralization steps (e.g., adding a base such as KOH to the polyol) can alter the characteristics of the polyol such that its use results in sub-optimal polyurethanes.

Finally, hydrogen peroxide can be explosive under certain conditions and care must be taken to ensure the safety of workers in hydroxylation processes that use hydrogen peroxide as the oxidizing agent for opening the C=C bonds in the fatty acid moieties.

Accordingly, there is a need for a simple, economical, safe, and efficient process for the preparation of polyols that are derived by opening the C=C of the fatty acid moieties of animal fats to add hydroxyl groups. In addition, there is a need for simple, economical, safe, and efficiently made animal fat derived polyols that possess a relatively low acid number to allow their use in urethane systems without further neutralization steps.

Described herein is a simple, safe, and economical preparative process for the provision of hydroxyl functional polyols of low acid number that are suitable for the formation of polyurethanes, wherein the polyols are derived by opening the alkene groups (C=C bonds) of the unsaturated fatty acid moieties of animal fats and adding hydroxyl groups. Also described herein is a unique polyol that is well suited for use in polyurethane applications.

In some embodiments, described herein are processes that begin by contacting triglycerides, which comprise triglycerides derived from animal fats, with hydrogen peroxide and an organic acid forming intermediate epoxide functionalities on a portion of the carbon-carbon double bonds of the unsaturated fatty acid carbon chains. This is followed by a ring opening reaction of the formed epoxide groups by nucleophiles like water, carboxylic acids, alcohols and amines. The result is the hydroxylation of the unsaturated fatty triglycerides which have been successful in polyurethane formulations as replacements or partial replacements of the polyether polyols that are widely used.

General Description of the Manufacturing Process

One aspect described herein is a process of making hydroxy functional animal fat by adding raw animal fat (and optionally a vegetable oil) and an organic acid or peracid in a reactor to form an organic phase and an aqueous phase. The organic phase and aqueous phase are heated with agitation to generate a hot mixture. Hydrogen peroxide is added to the hot mixture to create a reaction mixture. The reaction mixture is heated for a sufficient time, so as to form hydroxyl groups from unsaturated moieties in the animal fat. The reaction mixture is then subjected to a first purification step to separate volatiles from the hydroxylated functional animal fat. This produces a hydroxyl functional animal fat that tests for an acid number of about less than 10 mg KOH/g. A second purification step may be used to further reduce the acid number of the hydroxyl functional animal fat to less than 6 mg KOH/g, preferably to less than 4 mg KOH/g, more preferably to less than 2 mg KOH/g, or most preferably less than 1 mg KOH/g.

In another aspect described herein is the polyol comprising a reaction product of a raw animal fat, hydrogen peroxide, and an organic acid. In some embodiments the polyol comprises a reaction product of an animal fat, water, hydrogen peroxide, and an organic acid. The organic acid may be a mixture of a carboxylic acid and a peracid. The carboxylic acid may be formic acid, acetic acid, propionic acid, or lactic acid. In certain embodiments, the polyol further comprises a vegetable oil derived polyol.

In certain aspects, described herein is a process that converts an epoxidized animal fat into a polyol by reacting the epoxidized animal fat or a mixture of one or more epoxidized animal fats and optionally one or more vegetable oils with a nucleophile. In some embodiments, the nucleophile is water, an alcohol, a primary amine, a secondary amine, or an organic acid. In certain embodiments, the nucleophile reacts with the epoxidized animal fat in the presence of a catalyst.

In another aspect described herein is the polyol comprising a reaction product of an epoxidized animal fat and a nucleophile. In some embodiments, the nucleophile is water, an alcohol, an amine, or an organic acid. In some embodiments, the polyol further comprises a vegetable oil derived polyol.

For instance, Equation 1 of FIG. 1, depicts the formation of a peracid from the reaction of hydrogen peroxide and an organic acid, for example, acetic acid. Thereafter, the peracid reacts with carbon double bonds that are present in unsaturated animal fats to form an epoxide ring and regenerating the catalytic organic acid (Equation 2 of FIG. 1). Thereafter, the epoxide ring of the epoxidized triglyceride is opened by the influence of an organic acid to form the hydroxy ester as is shown in equation 3. Alternatively, the epoxide ring is opened by water to form diols (Equation 4 of FIG. 1) or even by previously formed hydroxyl groups to form a hydroxyl ether (not shown), or other nucleophiles. In certain instances, some epoxide rings remain in the final polyol product.

In some embodiments, the fats are combined with a predetermined amount of hydrogen peroxide and organic acid which converts a portion of the unsaturated carbon-carbon double bonds into epoxy groups, and then a portion of the epoxy groups into hydroxy groups. The amount of conversion of the above-mentioned functional groups is dependent on the amounts and ratios of the hydrogen peroxide and acid, and on the time and temperature of the reaction.

In certain embodiments, what is disclosed and claimed herein is a process for the preparation of organic intermediates from animal fats and oils that contain a combination of epoxy groups, hydroxy groups, and unsaturated alkene groups wherein the process can be utilized to control the amounts of each of the functional groups in the final product.

Animal Fats and Oils

Disclosed herein are novel processes for preparing hydroxy functional animal fats. Animal fats have been familiar to man since prehistoric times and for centuries humans have used animal based fats and oils for food and a variety of other uses.

In some embodiments, the terms animal fats, animal oils, animal lipids, as used herein, are interchangeable and encompass raw animal fat that has been obtained by normal processing techniques. In some embodiments, an animal fat is a solid animal fat. In other embodiments, an animal fat is a liquid animal oil. The animal fat may be crude, refined, bleached, deodorized, winterized, partially hydrogenated, bodied, or a modified hybrid. The term animal fat may include, by way of non-limiting examples, chicken fat, duck fat, turkey fat, goose fat, beef tallow, schmaltz, suet, ghee, mutton tallow, lard, fish oils, or any combinations thereof. Further, the term animal fat may include animal fat combined with any other triglyceride from any other source, including a combination of two or more different types of animal fat, any combination of animal fat and vegetable oil, or any combination of animal fat with a triglyceride from any other source.

Animal fats are made up principally of triglycerides containing both saturated and unsaturated fatty acid moieties, wherein the predominant moiety is the unsaturated variety (i.e., the variety having double bond carbon-carbon linkages (C=C) along the fatty acid carbon chain). Even though triglycerides are useful in many chemical applications, there are applications in which their performance can be improved if they are altered to have functionalities different than those that are found in the raw animal fat.

In order to use animal fats as feedstock in polyurethane processes, multiple hydroxyl functionality is required. Described herein the hydroxylation of unsaturated animal fats via epoxidation or oxidation of the C=C bonds using hydrogen peroxide ($H_2O_2$) followed by ring-opening of the resulting epoxides with proton donors.

Vegetable Oils

In some embodiments, the terms vegetable oil and plant oil are interchangeable and encompass raw vegetable oil that has been obtained by normal processing techniques without any modification to the chemistry of the oil itself (i.e. the oil has not undergone any substantive chemical treatment to alter its level of saturation or unsaturation after its initial production). The vegetable oil may be crude, refined, bleached, deodorized, winterized, partially hydrogenated, bodied, or a modified hybrid. The term vegetable oil includes, by way of non-limiting examples, corn oil, palm oil, palm kernel oil, soybean oil, cottonseed oil, peanut oil, rapeseed oil, safflower oil, canola oil, olive oil, rice bran oil, sunflower oil, jatropha oil, camelina sativa oil, and algae oil. Additionally, in some embodiments, the term vegetable oil may include the combination of vegetable oil with animal oil or any other triglyceride.

Triglycerides

In some embodiments, the term triglyceride encompasses structures formed by combining glycerol with three fatty acids. Most natural fats contain many different types of individual triglycerides. This complex mixture of individual triglycerides gives different types of fats different properties, for example, melting temperature.

Fat Saturation

The process described herein uses animal fats, or other triglycerides, having at least one percent (1%) unsaturation. Table I lists, by way of non-limiting example, fats and oils, and their corresponding iodine values that may be used in this invention. Here, the iodine value is the mass of iodine, in grams, that is consumed by 100 grams of fat. The iodine value is often used to determine the amount of unsaturation in fatty acids.

TABLE I

Fats and their Iodine Values

| Fat | Iodine Value |
|---|---|
| Ghee | 28 |
| Mutton tallow | 40 |
| Lard | 43 |
| Duck fat | 45 |
| Beef tallow | 50 |
| Palm oil | 54 |
| Turkey fat | 67 |
| Chicken fat | 80 |
| Olive oil | 81 |
| Castor oil | 85 |
| Peanut oil | 93 |
| Rapeseed oil | 98 |
| Cotton seed oil | 105 |
| Crude Fish oil | 109 |
| Sunflower oil | 125 |
| Soybean oil | 130 |
| Canola oil | 118 |
| Tung oil | 168 |
| Linseed oil | 190 |
| Camelina oil | 150 |
| Sardine oil | 185 |

Hydrogen Peroxide

Figure 2:
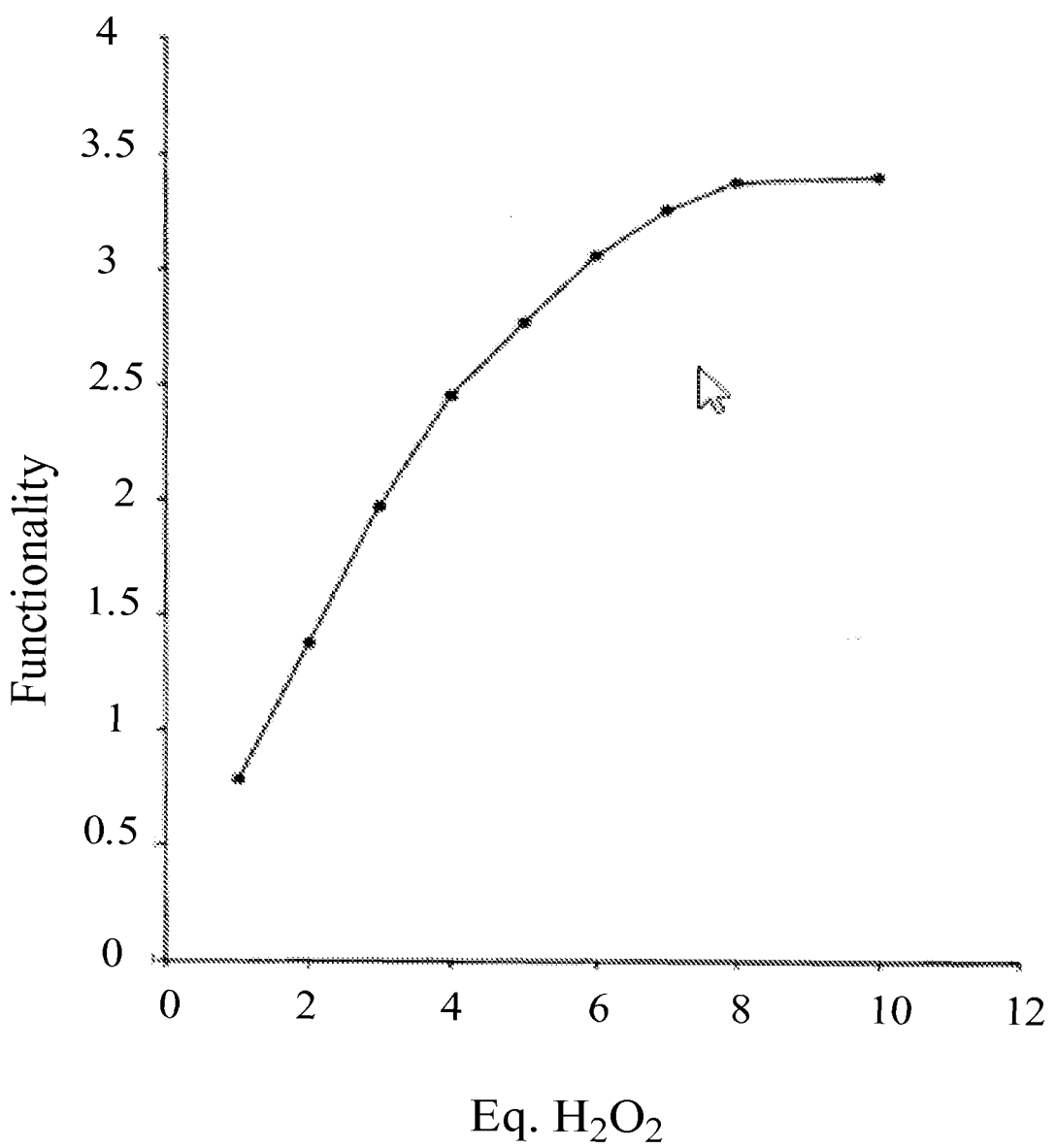
FIG. 2 is a graph of hydroxyl functionality versus the equivalents of peroxide used in the reaction to show the effect of excess peroxide.

In the process described herein, animal fat, hydrogen peroxide, and an organic acid or peracid are combined in the presence of water. The water in the reaction comes primarily from the aqueous hydrogen peroxide that is used. At lower concentrations of hydrogen peroxide, more water is added to the system which increases the amount of water that must be removed in a later purification step. In most instances practitioners should find that a 35% solution of hydrogen peroxide works well in the practice of the invention. The molar amount of hydrogen peroxide used determines the molar amount of peracid formed. The amount of peracid, in turn, determines the amount of unsaturated fat converted into epoxide, then into a hydroxyl compound. The amount of hydrogen peroxide used ranges from about 0.1 to about 6.0 moles of hydrogen peroxide per mole of animal fat. The amount and concentration of hydrogen peroxide used determines the amount of hydroxyl functionality in the final product. The effect of using larger amounts of the peroxide is illustrated in FIG. 2.

High strength hydrogen peroxide solutions (80% or greater) are very insensitive; explosions are difficult to initiate. In contrast, high strength hydrogen peroxide/organic mixtures can be extremely sensitive; they pose a high risk for exploding. Moderate strength (lower limit 45%) hydrogen peroxide/organic mixtures can also be explosive. In some embodiments, the concentration of the hydrogen peroxide is about 25-85% w/w, about 35-70% w/w, about 25% w/w, about 35% w/w, about 50% w/w, or about 70% w/w.

Figure 3:
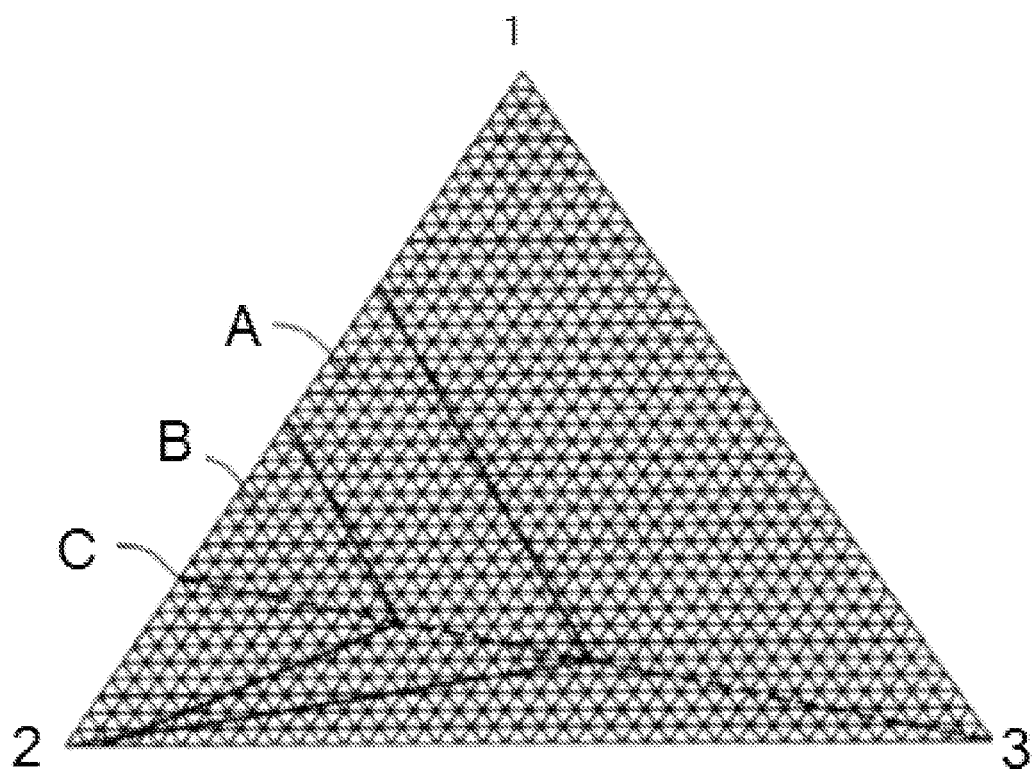
FIG. 3 is a triangular graph showing different explodable regions for peroxide systems.

The triangular graph shown in FIG. 3 shows different regions for hydrogen peroxide/organic mixtures, wherein A is the explosive region, B is the detonation region, and C is the stoichiometric line. Also shown are the designations 1 for the organic apex, 2 for the hydrogen peroxide apex, and 3 for the water apex. The stoichiometric line joins the hydrogen peroxide/organic baseline with 100% water through the apex of the explosive area. Explosive power of the mixtures decreases as the composition moves away from the stoichiometric line.

Figure 4:
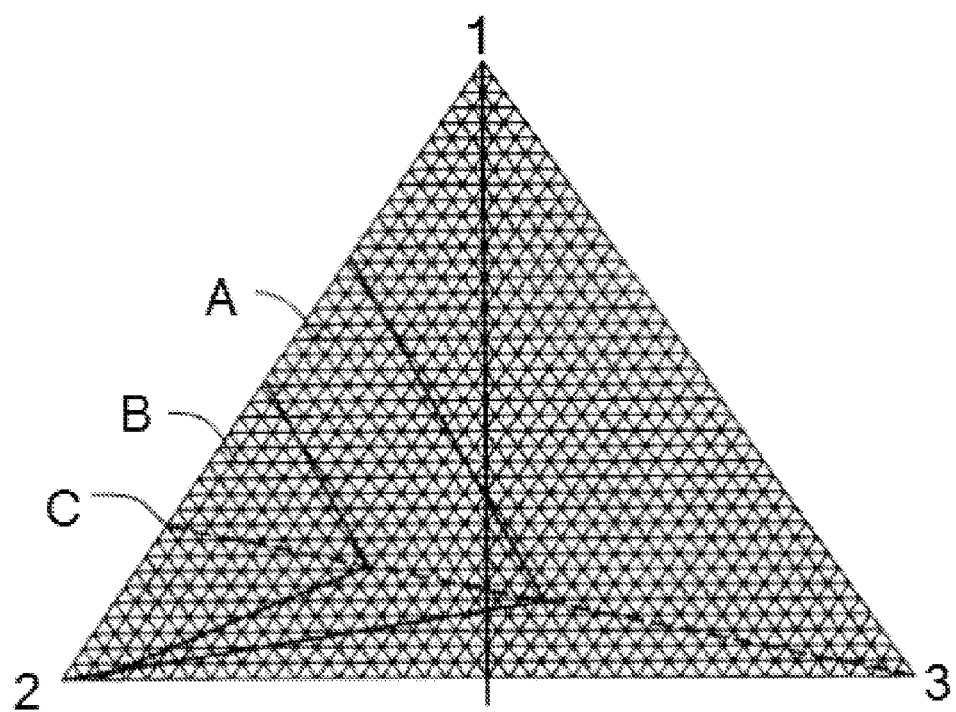
FIG. 4 is a triangular graph of 50% hydrogen peroxide and 100% concentration of organic solvent.
Figure 5:
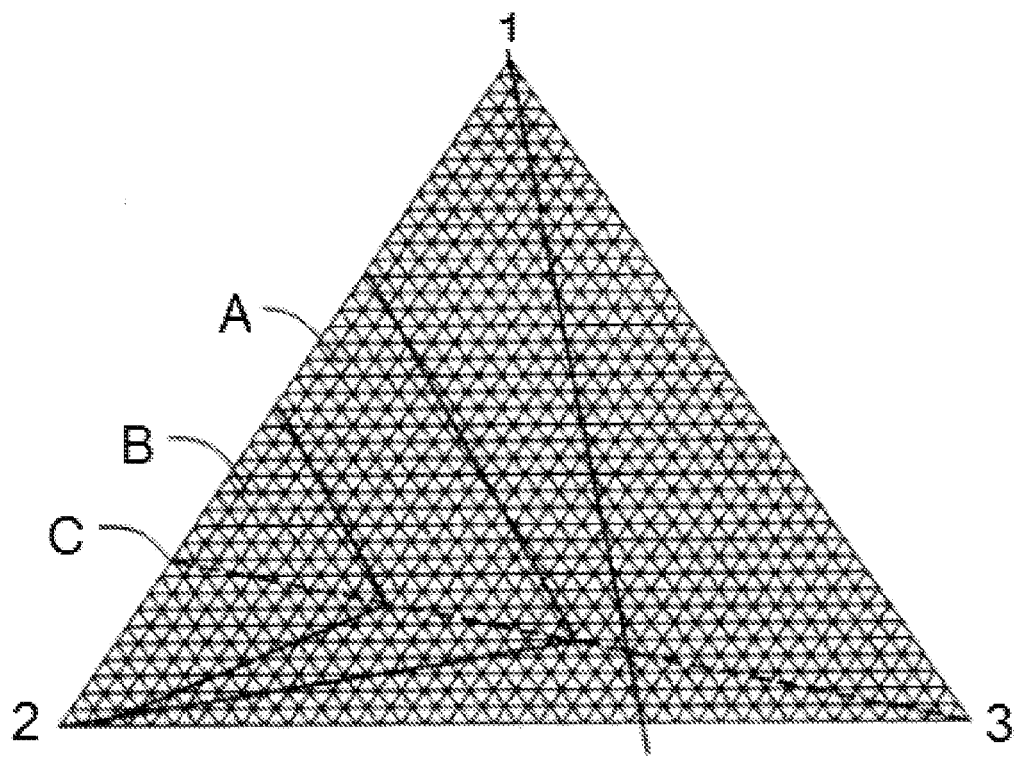
FIG. 5 is a triangular graph of 30% hydrogen peroxide and 100% concentration of organic solvent.

The mixture compositions may be determined by drawing a line between the concentration of the organic solvent and the initial concentration of the hydrogen peroxide. The FIG. 4 shows the mixture composition of 50% initial concentration of hydrogen peroxide and 100% concentration organic solvent, wherein A, B, C, 1, 2, and 3 are as designated. As shown, this line passes through the explosive region and is potentially hazardous. To avoid potential explosive mixtures, the hydrogen peroxide is diluted from 50% concentration to 30% concentration by adding water first before it is mixed with organic solvents as shown in the FIG. 5 wherein A, B, C, 1, 2, and 3 are as designated just above. The non-explosive regions as shown in the Figures are outside of the explosive regions and are the "safe" regions.

In some embodiments, the hydrogen peroxide may be substituted with other sources oxidation agents, including ozone, hypochlorite, peracids (such as performic acid, peracetic acid, and mCPBA [meta-chloroperoxybenzoic acid]).

Organic Acid

In some embodiments of the processes described herein, an organic acid is added to the animal fat. As used herein, the term organic refers to mean an organic acid of the general structure RCOOH. In certain embodiments, the organic acid has from 1 to 18 carbon atoms. In some embodiments, the organic acid is a carboxylic acid having 1 to 3 carbon atoms, mixtures of such acids, and mixtures of other acids wherein organic acids having 1 to 3 carbon atoms are the primary components. In certain embodiments, the term organic acid comprises formic, acetic, propionic acid, or lactic acid. Formic and acetic acid, particularly glacial acetic acid, are the preferred acids for use in the practice of the invention. Using acetic acid as a model organic acid in the examples should not be interpreted as limiting the scope of the invention. In some embodiments, the organic acid used in the processes described herein is a mixture of carboxylic acids with various number of carbons. In certain embodiments, as R in RCOOH becomes larger, or the mixture of carboxylic acids comprises more carboxylic acids with a large R group, the viscosity of the polyol product decreases at no cost to functionality of the resultant polyol.

The amount of organic acid used is tied to the amount of raw animal fat such that, the molar ratio of organic acid to animal fat preferably ranges from about 0.5:1 to about 10:1. The organic acid may be used in the ring opening reaction and as a solvent.

In some embodiments, a mineral acid such as sulfuric acid is used as a catalyst.

Peracid

Peracid is the peroxy form of an organic acid, or in other words, an acid in which an OOH group replaces an OH group. For instance, peracetic acid is a transparent, faint blue colored liquid that has a piercing odor and a pH of about 2.8. The peracid may be added exogenously or may be generated in situ by adding hydrogen peroxide to the organic phase of the animal fat and organic acid mixture. If peracid is generated in situ, the reaction mixture should be heated to about 85-110° C., with aging under reflux, in order to take the reaction to completion. The process, described herein, may be performed with a mixture of organic acid and hydrogen peroxide, peracids, or mixtures thereof.

Order of Ingredients

One option for the addition of ingredients to the reactor is adding fat, followed by the simultaneous addition of acid and hydrogen peroxide. A second option is fat, followed by acid and finally hydrogen peroxide. The third option is the simultaneous addition of fat, acid, and hydrogen peroxide. In the first two cases the acid and oxidant are metered in. In the third option, the fat, acid, and hydrogen peroxide are all metered in.

The order of addition of the components is not crucial to the practice of the invention. The animal fat may be one of several different oils, fats, triglycerides, or mixtures thereof, and components can be combined essentially simultaneously or in sequence, where either the organic acid or the hydrogen peroxide is added first. In the continuous process embodiment the components are essentially fed simultaneously.

Solvent

In some embodiments, a variety of solvents may be used in the process. Any aprotic solvent may be used other than ethers, as they have been shown to form explosive peroxides.

Reaction Vessels

In some embodiments, reactions and procedures should be carried out in a glass lined reactor, or an unreactive metal alloy reactor such as 316 L stainless steel, due to the hydrogen peroxide and organic acid used in the process. The vessel should be made of a material that does not impart a color to the product. If a 304 or 316L stainless steel reactor is used, it should be passivated before use.

In some embodiments, the reaction vessel must have heating, cooling, stirring, and venting capabilities. Further, the reaction vessel system must have the ability to seal and handle subsurface inert gases and system upset from the possible decomposition of hydrogen peroxide.

Passivation

Passivation, as used herein, consists of cleaning the stainless steel reaction vessel with distilled water and following with a detergent solution at about 49-52° C. At room-temperature, 5% w/w sodium hydroxide/water solution is then added and the surface is pickled for one hour. Then nitric acid (30-35% weight aqueous) is added to the reactor, aged for about 2 hours at room temperature with agitation, and washed with distilled water. A 5% hydrogen peroxide solution is added to the reactor and it is checked for degradation. If no degradation is observed, the hydrogen peroxide is removed and the reactor is ready for use. If the reactor is used for some other type of reaction, the passivation procedure should be repeated.

Reaction Time

In some embodiments, reaction time means between 30 minutes to 168 hours, the time anticipated to allow the hydroxylation reaction to occur. In certain embodiments, the reaction time is between 1-100 hours, 1-75 hours, 1-50 hours, 1-24 hours, including increments therein. Some of the beneficial properties of the intermediates, such as high hydroxyl number and controlled epoxide content, derive from the reaction sequence, wherein the materials are heated for 30 minutes to 168 hours, with stirring.

Reaction Temperature

In some embodiments, the reaction mixture's reaction temperature is greater than 40° C. In certain embodiments the reaction is performed under an inert atmosphere. In other embodiments, the reaction temperature is between about 50-150° C., between about 85-120° C., between about 85-110° C., between about 120-135° C., between about 105-115° C., between about 100-110° C., or between about 80-90° C. In certain embodiments, the heating and adding steps may be performed simultaneously or sequentially.

First Purification Step

In some embodiments, the first purification step comprises separating hydroxy functional polyols from volatiles at or around the reaction temperature, preferably less than 170° C.

In some embodiments, the first purification step uses temperatures between about 50-135° C. In other embodiments, the first purification step occurs at a temperature between about 60-140° C., between about 90-150° C., between about 90-140° C., between about 90-130° C., between about 70-135° C., between about 75-125° C., between about 75-90° C., between about 80-105° C., between about 50-90° C., between about 110-140° C., between about 80-110° C., or between about 105-115° C. In some embodiments, the first purification step occurs under vacuum. In some embodiments, the first purification step includes sparging with nitrogen, steam, air or other non-reactive gas. This purification step produces a hydroxyl functional polyol that tests for an acid number of about 10 mg KOH/g or less. In certain embodiments, the organic layer is separated from the aqueous layer before subjecting the organic layer to the first purification.

Second Purification Step

In some embodiments, an optional second purification step comprises separating hydroxy functional polyols from high boiling impurities and organic acids at a temperature above the reaction temperature, preferably less than 270° C. In certain embodiments, the second purification step uses a temperature of less than 150° C., between about 75-135° C., between about 75-110° C., between about 90-120° C., or between about 120-150° C. In other embodiments, the second purification step uses temperatures between about 170-270° C., between about 200-260° C., between about 220-260° C., or between about 235-255. In some embodiments, the second purification step occurs under vacuum. In certain embodiments, the second purification step includes sparging, wiped film evaporation, short path distillation, packed column stripping, or a combination thereof. The second purification step produces a hydroxy functional polyol with acid numbers of about 6 mg KOH/g or less, preferably about 4 mg KOH/g or less, more preferably about 2 mg KOH/g or less, or most preferably about 1 mg KOH/g or less.

Additional Purification Step

In some embodiments, an optional additional purification is used for the deodorization of the polyol product. This purification step may be performed after either the first or second purification steps. In certain embodiments, the additional purification step comprises sparging, wiped film evaporation, short path distillation, packed column stripping, or a combination thereof.

Sparging

In some embodiments of the processes described herein, the reaction mixture and/or the hydroxy functional polyol is subjected to sparging. In certain embodiments, sparging is comprised of introducing a chemically inert gas, such as nitrogen, into a liquid. In other embodiments, sparging is comprised of introducing steam or air into the liquid. In some embodiments, sparging is performed in the first, second, and/or additional purification steps, including any combinations therein. In some embodiments, the sparging occurs at a rate of 0.1-10 standard cubic foot/hour/100 pounds of product, and more preferably at a rate of 1-5 standard cubic foot/hour/100 pounds of product.

Some of the beneficial properties of the intermediates, such as low odor, low color, low water content derive from concentrating and deodorizing the product, using vacuum and sparging at a temperature of about 90-130° C. Preferred embodiments keep the temperature closer to 90° C. in order to avoid the appearance of color. The concentration and deodorization step results in lower levels of decomposition products such as aldehydes and ketones which are present in other preparation processes.

Pressure

In some embodiments, the purification is performed under vacuum. In certain embodiments, the purification with sparging is performed under a vacuum. In some embodiments, the pressure required during purification is 80 mmHg or less. In other embodiments, the pressure required during purification is less than 60 mmHg, less than 50 mmHg, less than 20 mmHg, or less than 14 mmHg. In certain embodiments, the pressure required during the purification is a high vacuum of less than 1 mmHg.

Polyols Created by the Methods and Processes Described Herein

In some embodiments, the hydroxylated animal fats are polyols with acid numbers less than 10 mg KOH/g after the first purification step, less than 6 mg KOH/g, more preferably less than 4 mg KOH/g, most preferably less than 2 mg KOH/g after further purification steps, using American Oil Chemists' Society (AOCS) Official Process, Cd 3d-63 for obtaining the acid value.

In some embodiments, the hydroxylated animal fats are polyols having a final epoxide range up to 4.1% w/w, more preferably up to 3.5% w/w, most preferably up to 3.0%.

In some embodiments, the hydroxylated animal fats are polyols having no residual peroxygens, less than 0.1% w/w of water, and less than 0.1% w/w of organic acids.

In some embodiments, the hydroxylated animal fats are polyols having a viscosity between 200 to 32,000 cP and can be controlled either by the controlled oxidation of the animal fat, or by the length of the carbon chain on the acid that becomes part of the ester portion of the molecule in the product. Thus, as R in RCOOH becomes larger, the viscosity decreases at no cost to functionality of the resultant polyol.

Hydroxyl Number

Hydroxylation is the introduction of a hydroxyl group (—OH) into an organic compound. The AOCS Official Process, Cd 13-60, was used to obtain hydroxyl numbers. In some embodiments, the hydroxyl number of animal fat derived polyols is up to about 230. In certain embodiments, the hydroxyl number of mixtures of animal fat and vegetable oil derived polyols is up to about 230. In some embodiments, the hydroxyl number of animal fat derived polyols is about 65-75, about 107-117, or about 125-137. In certain embodiments, the hydroxyl number of mixtures of animal fat and vegetable oil derived polyols is about 65-75, about 107-117, about 125-140, or about 151-190 mg KOH/g.

Acid Number

The animal fat derived polyols described herein are purified to an acid number of about 10 mg KOH/g or less. In other embodiments, the acid number is less than 6 mg KOH/g, preferably less than 4 mg KOH/g, more preferably less than 2 mg KOH/g, or most preferably less than 1 mg KOH/g.

Low Odor

In some embodiments, the polyols produced by the processes described herein and polyurethane foams produced therefrom are described as low odor. Some commercially offered soy-based polyols and polyurethane foams produced therefrom suffer from having an odor that is best described as simply characteristic of soybean oil. This odor is easily detected by the human nose and has been compared to stale French fries or old, used cooking oil. The odor can be found in neat liquid soy polyol and transfers to the foam articles made using such polyols. The odor inherent in soy-based polyols is one factor such polyols have not had widespread and long-running commercial success.

Polyurethanes

In some embodiments, the animal fat derived polyol is particularly suitable for making a variety of polyurethane products, for example, reaction injection molding, castable elastomers, and any of the traditional molded or free rise flexible and rigid foams. Such products include "high density" (>20 pcf) or "low density" (≤6 pcf) foams. These foams are often used in construction applications, e.g., spray applied or laminate insulation or for the formation of articles such as ornamental pieces, bun stock, and molded or pour-in-place parts. In short, the claimed polyol may be used to manufacture any product typically made from urethane systems that utilize petroleum-based polyether and polyester polyols.

In certain embodiments, the hydroxylated animal fat polyols are reacted with isocyanates to form polyurethanes. The polyurethanes can have a number of commercial applications, including foams, potting compounds, cast resins, coatings, elastomers, adhesives, sealants, composites, non-reinforced and fiber reinforced plastics processed using resin transfer molding (RTM), and reaction injection molding (RIM), filament winding, and pultrusion techniques.

Non-Limiting Exemplary Processes and Products
General Method of Single Batch Processing of Hydroxy Functional Animal Fats This section outlines the method, in general terms, for single batch processing of hydroxylation of functional animal fats.

Predetermined amounts of reaction components (animal fat, hydrogen peroxide, and organic acid) react at a sufficient temperature for a minimum of one hour. In most instances, the initial reaction proceeds until residual epoxide level is less than or equal to 1.5% (≤1.5%) w/w of oxirane oxygen.

After the reaction has reached the desired conversion point, the crude polyol product is separated from volatiles in a first purification step, using any number of different means known to those skilled in the art. For example, the crude polyol product may be heated in a flash tank under vacuum. Alternatively, a wiped film evaporator may be used to conduct this initial purification step. Those skilled in the art are capable of designing other mechanical systems to accomplish this step; such systems are within the overall scope of this process. Further, those skilled in the art recognize that temperature and level of vacuum applied share an inverse relationship; therefore there are multiple combinations of temperature/pressure that may be used in the practice of this step. After the initial purification step, the semi-refined polyol product is heated to remove and/or react any remaining fatty acids in the polyol.

As with the initial purification step, the second purification step may be practiced in a number of ways. The equipment used may include, by way of non-limiting example, reactors, high temperature vacuum strip reactors, wipe film evaporators, falling film columns, counter current packed columns, steam stripping vessels, or distillation. Likewise, the time, temperature, and pressure may vary depending upon the equipment used.

After obtaining a refined polyol product, an antioxidant may be added and the product filtered via a 100 to 250 micron filter, before transferring to storage.

Method of Preparing Hydroxy Functional Animal Fats Using a Pressure Reactor and Nitrogen Sparging Described herein, in certain embodiments, is a process of preparing hydroxy functional animal fats, comprising adding raw animal fat to acetic acid in a pressure reactor, capable of being sealed, to form an organic phase and an aqueous phase; sealing the reactor and heating to about 85-120° C. with agitation; metering 25 to 70% weight/weight of hydrogen peroxide/water to the hot mixture; keeping the hot mixture at about 85-120° C., with 0 to 25 psig pressure, to generate peracid; heating the reaction mixture to about 120-135° C., under a pressure of about 12-45 psig for about 1.5 to 3 hours, and then cooling the mixture to about 50-90° C. without agitation; removing the aqueous phase from the pressure reactor; stripping the bulk of the acetic acid from the organic phase, aqueous phase, and other low boilers at 90-150° C. and 5 to 60 mm Hg; applying a negative pressure of about 2 to 15 mm Hg under a nitrogen sparge; heating the materials to about 220-260° C. until the reaction mixture tests for an acid number of about 2 mg KOH/g or less. An antioxidant may then be added followed by filtration through 100 to 250 micron filter media before transferring to storage.

Method of Preparing Hydroxy Functional Animal Fats Using Two Purification Steps with Nitrogen Sparging Described herein, in certain embodiments, is a process of preparing a hydroxy functional animal fat, comprising: combining raw animal fat, hydrogen peroxide, and an organic acid in the presence of water for a sufficient period of time, temperature, and pressure to form hydroxyl groups from unsaturated moieties in the animal fat; separating any volatiles from the hydroxylated functional animal fat at a temperature of about 90-150° C.; charging the product to a distillation vessel equipped with a condenser and distillate receiver, in which the vessel remains 85-90% by volume full; agitating the product and applying a negative pressure of about 5 to 60 mm Hg to the vessel; heating the vessel to about 90-140° C. and holding at that temperature until the distillate ceases; sparging with nitrogen at about 2 to 8 standard cubic foot/hour/100 pounds of product to strip the volatiles; heating the product to 220-260° C. while removing distillate until the acid number of the product is about 2 mg KOH/g or less.

Preparation of Organic Reactive Intermediates

Preparing organic reactive intermediates involves using fatty acid chains cleaved from an animal fat triglyceride backbone or the methyl esters derived from the same as starting materials. All types of triglycerides may serve as suitable raw material for the claimed process and are considered to be within this scope of the process described herein. The process described herein creates triglyceride hybrids having variable levels of alkene, epoxide, and hydroxyl content.

In one embodiment, the process comprises combining predetermined amounts of animal fats in any form, having at least 1% by weight of unsaturation with predetermined amounts of hydrogen peroxide (preferably between 25% and 85% w/w) and organic acid (preferably between 80% and 100% w/w) in a reaction vessel. Formic and formic-derived peracid, as opposed to acetic and acetic-derived peracid, speed up the epoxide ring formation and also accelerate the epoxide ring opening to form hydroxy groups. Alternately, a mineral acid such as sulfuric acid may be used as a catalyst to accelerate the reaction. The reaction may be carried out at or near atmospheric pressure, with or without an inert blanket of gas, such as, nitrogen.

The mixture is then heated to at least 45° C., optionally under an inert atmosphere, for a period of time of 30 minutes to 168 hours, with stirring.

Thereafter, the product is concentrated and deodorized by vacuum and sparging, at a temperature of 90-130° C. to provide a product having an acid number less than 10 mg KOH/g, more preferably less than 6 mg KOH/g, more preferably less than 4 mg KOH/g, more preferably less than 2 mg KOH/g, more preferably less than 1 mg KOH/g, most preferably less than 0.5 mg KOH/g. It is preferred to keep the temperature closer to 90° C. in order to avoid coloring the polyol. The concentration and deodorization step results in lower levels of decomposition products such as aldehydes and ketones which are present in other preparation processes. The beneficial properties of the intermediates, such as low odor, low color, low water content come from this part of the concentration and deodorization step.

Epoxides in the final product range from 0.0 to 4.1% w/w. The preferred epoxide content ranges from 0.1 to 3.5% w/w. More preferred are epoxide ranges from 1.2 to 3.0%.

Figure 6:
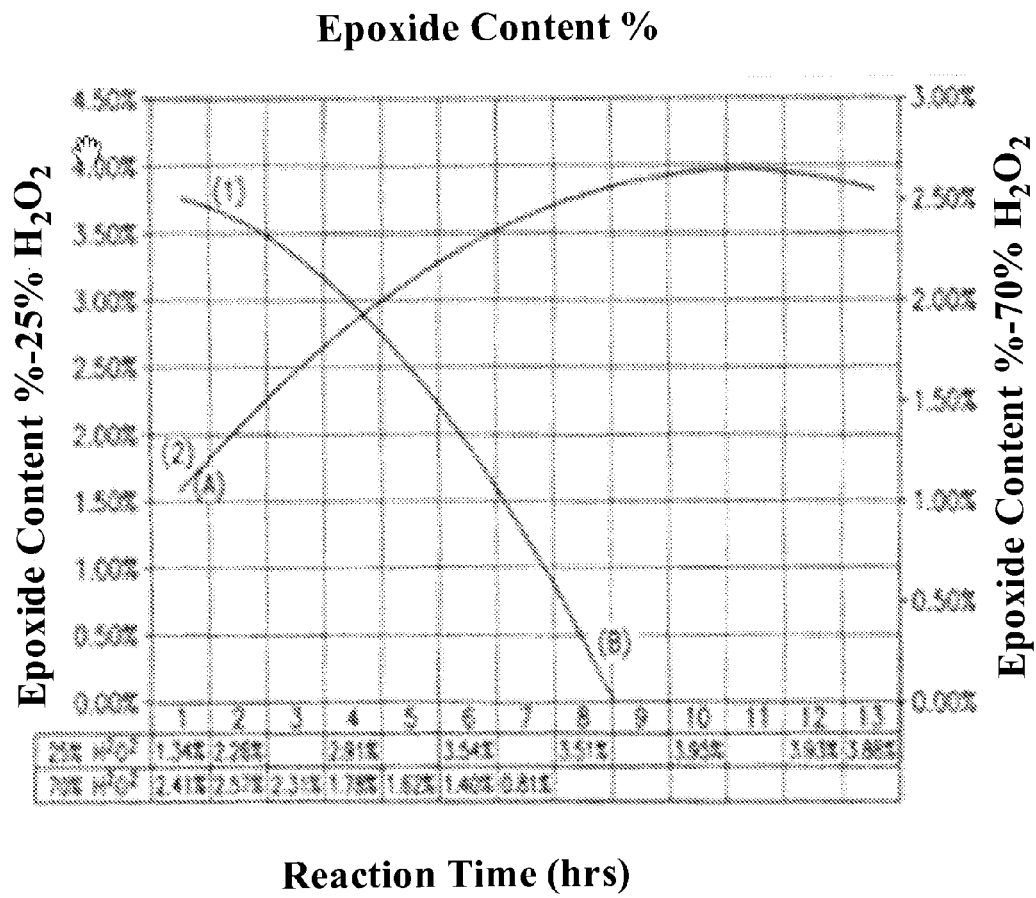
FIG. 6 is a graph to determine concentrations and ratios of reaction components that yield the desired number of functional groups.

In certain embodiments, the product does not have to be neutralized at any point during or after the reaction. The graph in FIG. 6 may help determine the concentrations and ratios of the reaction components needed to produce the approximate amounts of functional groups desired.

Method of Preparing Hydroxy Functional Animal Fats Using a Packed Column

Described herein, in certain embodiments, is a process of preparing hydroxy functional animal fats, comprising: combining animal fat, hydrogen peroxide, and organic acid in the presence of water for a sufficient period of time, temperature, and pressure to form hydroxyl groups from unsaturated moieties in the animal fats; separating the reaction mass into an aqueous phase and an organic phase containing the hydroxylated animal fats, removing volatiles from the organic phase at a temperature of less than 90-150° C. and a pressure of 5 to 60 mm Hg or less; heating the product to a temperature in the range of about 220-260° C. and moving the heated product downward through a packed column while forcing, under pressure, steam or non-reactive gas, upward through the packed column to remove high boiling impurities and organic acids; collecting the hydroxylated animal fats.

Method of Preparing Hydroxy Functional Animal Fats Using a Degasser and Wiped Film Evaporator Described herein, in certain embodiments, is a process of preparing hydroxy functional animal fats, comprising: adding raw animal fat to acetic acid to form an organic phase; adding 25 to 70% w/w hydrogen peroxide to form an aqueous phase; heating the mixture to about 85-110° C. to generate peracetic acid in situ, and aging at that temperature under reflux; cooling the resulting material to 50-90° C.; allowing the aqueous phase and the organic phase to separate; separating the aqueous phase from the organic phase; heating a degasser (flash evaporator) to at least 50-90° C. with a pressure of 5 to 15 mm Hg; moving the organic phase into the degasser; flashing off the majority of the residual acetic acid and aqueous phase; feeding the semi-purified product to a first wiped film evaporator at a temperature of about 60-140° C., pressure of about 5 to 20 mm Hg, wipe speed of about 300 to 350 rpm, and a feed flow rate of about 25 to 45 pounds per hour, while maintaining the internal condenser temperature at about 0-12° C.; feeding the purified product to a second wiped film evaporator at a temperature of about 220-260° C., at a pressure of about 0.001 to 0.003 mmHg, wipe speed at about 300 to 350 rpm and a feed flow rate of about 25 to 45 pounds per hour, while maintaining the internal condenser temperature at about 35-70° C.; cooling and recovering a product with an acid number less than about 2 mg KOH/g; adding an antioxidant and filtering via a 100 to 250 micron filter before transferring the product to storage.

Method of Preparing Hydroxy Functional Animal Fats Using a Degasser, a Fractional Distillation Column, and a Wiped Film Evaporator Described herein, in certain embodiments, is a process of preparing hydroxy functional animal fat, comprising: adding raw animal fat to acetic acid to form an organic phase; combining hydrogen peroxide and acetic acid in water to form an aqueous phase; adding the aqueous phase to the organic phase, keeping the amount of hydrogen peroxide in the safe region; cooling the resulting material to less than 50-90° C. and allowing the organic phase and the aqueous phase to separate; separating the aqueous phase from the organic phase; moving the aqueous phase to a holding tank and then recycling the aqueous phase; heating a degasser to at least 50-90° C. with a pressure of 5 to 15 mm Hg moving the organic phase into the degasser; flashing off the majority of the residual acetic acid and aqueous phase and feeding the residual acetic acid and aqueous phase to a fractional distillation column for recovery and recycling; feeding the purified product to a first wiped film evaporator at a temperature of about 60-140° C., with a pressure of about 5 to 15 mmHg, wipe speed of about 300 to 350 rpm, and a feed flow rate of about 25 to 45 pounds per hour, while maintaining the internal condenser temperature at about 0-12° C.; collecting the evaporate in an acid holding tank; feeding the product to a second wiped film evaporator at a temperature of about 220-250° C., pressure of about 0.001 to 0.003 mmHg, wipe speed at about 300 to 350 rpm and a feed flow rate of about 25 to 45 pounds per hour, while maintaining the internal condenser temperature at about 35-70° C.; collecting the evaporate in an acid holding tank; cooling and recovering the product; adding an antioxidant and filtering via a 100 to 250 micron filter before transferring the product to storage.

Method of Preparing Hydroxy Functional Animal Fats Using a Pressure Reactor, a Fractional Distillation Column, and Nitrogen Sparging Described herein, in certain embodiments, is a process of preparing hydroxy functional animal fat, comprising: adding raw animal fat to acetic acid in a pressure reactor to form an organic phase and an aqueous phase; sealing the reactor and heating to about 85-120° C. with agitation; metering 25-70% weight/weight of hydrogen peroxide/water to the hot mixture; heating the reaction mixture to about 120-135° C., under a pressure of about 12 to 45 psig for about 1.5 to 3.0 hours; cooling the mixture to about 50-90° C. without agitation; separating the aqueous phase and moving to a distillation column for the recovery of the acetic acid; stripping off bulk of the acetic acid, aqueous phase and other low boilers from the product at 90-150° C. and 5 to 60 mm Hg; moving the acetic acid, aqueous phase and other low boilers to a distillation column and recovering the acetic acid; applying a negative pressure of about 2 to 15 mm Hg under a nitrogen sparge and heating the materials to about 220-260° C. until the reaction mixture tests for an acid number less than about 2 mg KOH/g; collecting any acids removed from the product; adding an antioxidant and filtering via a 100 to 250 micron filter before transferring the product to storage.

General Continuous Process Hydroxylation

In addition to single batch processing of hydroxy functional animal fats, embodiments also encompass a method of preparing a hydroxy functional animal fat using a continuous process. In batch processing, all the raw materials are initially charged into the reactor, the reaction is conducted, and then the reactor is emptied of the product and recharged for a subsequent reaction. In a continuous process, however, there is a constant flow of raw materials into a reactor (e.g., a Continuous Stirred Tank Reactor (CSTR)), and the product is continuously produced and collected.

In some embodiments, the first stage of the continuous process comprises: continuously charging a reactor with animal fat, hydrogen peroxide, and organic acid or peracids, at a temperature sufficient to initiate the hydroxylation reaction. In preferred embodiments this temperature is above about 50° C., more preferably around 105° C., but may vary depending on the composition of the reaction mixture. The flow rate of reactants into the reactor should provide a residence time sufficient to achieve a crude polyol product having a residual epoxide level less than or equal to 1.5% (≤1.5%) w/w of oxirane oxygen. This flow rate will necessarily change depending upon the volume and equipment used. Those skilled in the art can make the necessary calculations to achieve a suitable residence time for their particular system.

In some embodiments, the second stage of the continuous process comprises continuously transferring the crude polyol product from the initial reactor to a purification step that encompasses both the bulk removal of any aqueous phase and the removal of low boiling volatiles. In this step, the crude polyol product is heated while under a vacuum. The level of heat and vacuum should be sufficient to remove the low boiling volatiles and achieve a semi-refined product. This step may be accomplished using any of several different pieces of separation equipment.

In some embodiments, the third stage of the continuous process comprises continuously transferring the semi-refined product of the volatile purification step to a further reaction step where the semi-refined product is subjected to heat while under vacuum wherein the heat and vacuum and residence time are sufficient to achieve a final polyol product having an acid number less not more than 2 mg KOH/g. As with the second stage, this further reaction step may be accomplished using any of several different pieces of equipment known to those skilled in the art and includes those discussed in relation to the further reaction step in the batch process embodiment of the invention.

Continuous Process Utilizing Continuous Stirred Tank Reactor (CSTR), and Vacuum Strip CSTR For example, in some embodiments, a CSTR reactor is first heated to the reflux temperature of the reactants (100-110° C.) as it is continuously charged with animal fat, hydrogen peroxide diluted to the required concentration, and organic acid having 1 to 3 carbon atoms. The flow rates of reactants are adjusted to allow enough residence time for the reactants to achieve residual epoxide level of ≤1.5% w/w of oxirane oxygen. Once the reactor is 90% full, the outflow from the first CSTR is fed into a second CSTR. At this stage the volume in the reactor achieves a steady state in which the continuous flow of reactants into the reactor equals the constant outflow of reaction mixture containing a crude polyol product into the second CSTR.

The second CSTR is maintained at 140-160° C. and 20-50 mm Hg, where the bulk of the organic acid and water are constantly distilled off the outflow from the first CSTR. The acid number of the polyol is reduced to about 6-10 mg KOH/g in the second CSTR.

A constant stream of semi-refined product is withdrawn from the second CSTR and is charged into a third CSTR maintained between 220-255° C. and at 5 to 10 mm Hg. The feed rate to this reactor is adjusted such that the residence time in this reactor allows for reduction of acid number not more than about 2 mg KOH/g. The overflow from the third CSTR is discharged into product storage tank, maintained under nitrogen padding, where the product is cooled to the packaging temperature (about 50° C.).

Continuous Process Utilizing CSTR, a Flash Tank, and a Wiped Film Evaporator

In some embodiments, the first step in the continuous process comprises: charging animal fat, hydrogen peroxide, diluted to the required concentration, and organic acid, continuously into a CSTR reactor maintained at reflux temperature (100-110° C.). The flow rates of the reactants are adjusted to allow enough residence time for the reactants to achieve residual epoxide level of ≤1.5% w/w of oxirane oxygen.

Once the reactor is 90% full and is at steady state, the outflow from the first CSTR is fed continuously through a flash evaporator maintained at 140-160° C. and 20 to 50 mm Hg. Most of the organic acid and water are flashed off the product stream from the first CSTR. The acid number of the resultant semi-refined product is about 6 to 10 mg KOH/g.

The semi-refined product is further fed into a wiped film evaporator maintained at 220-260° C. and ≤1 mmHg. The wiped film evaporator has a wipe speed of about 300 to 350 rpm and the internal condenser temperature is maintained between 35-70° C., which allows fatty acid to be collected into a fatty acid holding tank. The resulting product will have an acid number of not more than about 2 mg KOH/g and is further cooled and stored under nitrogen padding.

Continuous Process Utilizing CSTR, Vacuum Strip CSTR, and a Countercurrent Packed Column Fatty Acid Strip In some embodiments, a CSTR reactor is heated to the reflux temperature of the reactants (100-110° C.) and continuously charged with animal fat, hydrogen peroxide, diluted to the required concentration, and organic acid having 1 to 3 carbon atoms. The flow rates of reactants are adjusted to allow enough residence time for the reactants to achieve residual epoxide level of ≤1.5% w/w of oxirane oxygen.

Once the reactor is 90% full, the outflow from the first CSTR is fed into a second CSTR that is maintained at about 140-160° C. and 20 to 50 mm Hg, where the organic acid and water are continuously distilled off of the crude polyol product. The acid number of resulting semi-refined product is about 6 to 10 mg KOH/g in this CSTR.

A constant stream of semi-refined product is withdrawn from the second CSTR and further reacted at 220-260° C. by passing it through an inline heat exchanger. The heated product is passed downwardly through a packed column while steam or other inert gas is forced up through the column to remove/react high boiling fatty acids. The resulting polyol product will have an acid number not more than 4 mg KOH/g.

Continuous Process Utilizing CSTR, Vacuum Strip CSTR, and Steam Stripping Reactor In some embodiments, a CSTR reactor is heated to the reflux temperature of the reactants (100-110° C.) and continuously charged with animal fat, hydrogen peroxide, diluted to the required concentration, and organic acid having 1 to 3 carbon atoms. The flow rates of reactants are adjusted to allow enough residence time for the reactants to achieve residual epoxide level of ≤1.5% w/w of oxirane oxygen.

Once the reactor is 90% full, the outflow from the first CSTR is fed into a second CSTR maintained at about 140-160° C. and 20 to 50 mm Hg, where the organic acid and water are continuously distilled off of the crude polyol product. The acid number of resulting semi-refined product is about 6 to 10 mg KOH/g in this CSTR.

The semi-refined product leaving the vacuum strip CSTR is fed continuously into a third CSTR. The third CSTR semi-refined polyol product is maintained at 180° C. and sparged with steam to remove/react the high boiling fatty acids and reduce the acid number to 4 mg KOH/g or less.

Using the Hydroxylated Animal Fat in Urethane Chemistry

The polyols produced by the methods and processes described herein possess characteristics that are particularly well suited for manufacturing polyurethane articles. Accordingly, both the batch and continuous processes may comprise an additional step of reacting the final polyol product with an isocyanate in a urethane system to form a polyurethane. The polyurethane may be formed into an article, including, but not limited to foams, potting compounds, coatings, elastomers, sealants, composites, adhesives and both non-reinforced and fiber reinforced plastics processed using resin transfer molding (RTM), reaction injection molding (RIM), filament winding, and pultrusion techniques.

EXAMPLES

Example 1

Creating a Hydroxy Functional Animal Fat Using 50% Chicken Fat and 50% RBD Soybean Oil About 250 g of pure chicken fat (pet fat grade from Tyson Foods) and another 250 g of RBD (refined, bleached, and deodorized) grade soybean oil were added to a 1000 ml round bottomed flask, followed by about 104.8 g of glacial acetic acid (99% w/w conc.), 77.1 g of hydrogen peroxide (50% w/w conc.), and 33.04 g of water. The reaction was carried out by heating and maintaining the reaction mixture at 100° C. using a heating mantle. A sample of the reaction mixture was taken about 17 hours into the reaction and titrated for residual epoxide concentration. The residual epoxide obtained was 0.0536% w/w of oxirane oxygen, which equals to an epoxide conversion of 99.2%; the reaction was considered complete.

The reaction mixture was then purified by applying vacuum and distilling off excess water and acid left at the end of the reaction. Once the distillate flow ceases, the temperature of the reaction flask was slowly increased to about 235° C. When the temperature of the reaction flask reached 235° C., a sample was pulled and the acid number was 1.1 mg KOH/g. The product was then cooled to 70° C. The resulting polyol had a hydroxyl number of 106 mg KOH/g, viscosity of 980 cP, moisture content of 0.02% w/w, and an acid number of 1.1 mg KOH/g.

Example 2

Preparation of Polyurethane Foam Using a Polyol Derived from 50% Chicken Fat and 50% RBD Soybean Oil Two 1.7 pcf slabstock foams were prepared using hand-mix techniques. The control foam was prepared using a commercial soy-based polyol, Agrol® 3.6 (having a viscosity of 720 cPs, hydroxyl value of 112 mg KOH/g and an acid number of 0.4 mg KOH/g, available from BioBased Technologies LLC of Springdale, Ark.) and Arcol® F-3022, a petroleum based 3,000 molecular weight polyether triol, available from Bayer MaterialScience. The other foam was prepared using a renewable polyol of the invention (an hydroxylated polyol made with a 50/50 mixture of RBD soybean oil and pet food grade chicken fat from Tyson Foods, having a viscosity of 980 cP, hydroxyl value of 106 mg KOH/g and an acid number of 1.1 mg KOH/g) and Arcol® F-3022.

The B-side blend components (270 grams) were weighed into a 32 oz. cardboard bucket and premixed for 180 seconds at 3100 rpm. The required amount of TDI isocyanate was then added to the container and mixed at 3100 rpm for 6 seconds. The reaction mixture was then poured into 12×12×6 in. cardboard bakery boxes and the foam was allowed to rise. After 10 minutes, the foam was placed in a 120° C. oven for thirty minutes. The foams were then placed in a fume hood at room temperature for a 24 hour period before being cut for physical property measurements. The composition of the foam components in parts by weight are shown in the following table.

| Reaction Components | Control | Foam A |
| --- | --- | --- |
| Arcol ® F-3022 | 85 | 85 |
| Agrol ® 3.6 | 15 | |
| Soy/Chicken Polyol | | 15 |

-continued

| Reaction Components | Control | Foam A |
|---|---|---|
| Niax ® DP-1022 | 0.5 | 0.5 |
| Dabco ® 33LV | 0.04 | 0.04 |
| Niax ® A-1 | 0.04 | 0.04 |
| Niax ® L-595 | 0.70 | 0.70 |
| Water | 4.05 | 4.05 |
| Dabco ® T-9 | 0.18 | 0.18 |
| Toluene Diisocyanate | 49.16 | 49.05 |

Dabco® 33LV is a gel catalyst consisting of 33% triethylene diamine in 67% dipropylene glycol (from Air Products). Niax® A-1 is a blowing catalyst consisting of 70% bis(dimethylaminoethyl)ether and 30% dipropylene glycol (from Momemtive), Niax® L-595 is a silicone surfactant (from Momentive) and Dabco® T-9 is a stannous octoate gel catalyst (from Air Products). The toluene diisocyanate used is an 80/20 mixture of the 2,4 and 2,6 isomers from Bayer MaterialScience (Mondur® TD-80).

The physical properties of the foams of Example 2 are shown in the following table.

| Property | Control | Foam A |
|---|---|---|
| Density (pcf) | 1.70 | 1.71 |
| Air Flow (cfm) | 4.2 | 3.95 |
| Ball Rebound (%) | 26 | 27 |
| Comp. Set ($C_t$-50%) | 6.03 | 5.76 |
| 25% IFD (lb/50 in$^2$) | 32.72 | 31.27 |
| 65% IFD (lb/50 in$^2$) | 56.76 | 60.50 |
| Support Factor | 1.7 | 1.9 |
| Tensile Str. (psi) | 15.94 | 19.91 |
| Elongation (%) | 282 | 267 |
| Tear Strength (N/mm) | 0.78 | 0.86 |
| Hysteresis (%) | 80.9 | 77.4 |

Example 3

Creating a Hydroxy Functional Animal Fat Using 75% Chicken Fat and 25% RBD Soybean Oil In this experiment about 375 g of pure chicken fat (pet fat grade from Tyson Foods) and another 125 g of RBD (refined, bleached, and deodorized) grade soybean oil were added to a 1000 ml round bottomed flask, followed by addition of 104.8 g of glacial acetic acid (99% w/w conc.), 108.7 g of hydrogen peroxide (50% w/w conc.), and 46.6 g of water. The reaction was carried out by heating and maintaining the reaction mixture at 100-102° C. using a heating mantle. A sample of the reaction mixture was taken about 16 hours into the reaction and titrated for residual epoxide concentration. The residual epoxide obtained was 0.06% w/w of oxirane oxygen, which equals to an epoxide conversion of 99.1%; the reaction was considered complete.

The reaction mixture was then purified by applying vacuum and distilling off excess water and acid left at the end of the reaction below a temperature of about 150° C. Once the distillate flow ceases, the temperature of the reaction flask was slowly increased to about 235° C. and held at that temperature for about 4 hrs. At that time the acid number of the batch was tested to be at 2.1 mg KOH/g. The product was then cooled to 70° C. using nitrogen sparge. The resulting polyol had a hydroxyl number of 103 mg KOH/g, viscosity of 3190 cP, moisture content of 0.07% w/w, and an acid number of 1.7 mg KOH/g.

Example 4

Creating a Hydroxy Functional Animal Fat Using 100% Chicken Fat

The experiment was conducted in a 1000 ml, 3 neck round bottomed flask equipped with a thermocouple probe and a reflux condenser.

About 500 g of pure chicken fat (pet fat grade from Tyson Foods) was added to a 1000 ml round bottomed flask, followed by about 105.2 g of glacial acetic acid (99% w/w conc.), 82.1 g of hydrogen peroxide (50% w/w conc.), and 35 g of water. The flask was heated to 100° C. using a heating mantle. When the temperature reached about 100° C., it generated an exothermic reaction controlled by a reflux condenser and the contents are refluxed back into the reaction flask. Once the exotherm subsides, the temperature of the reaction mixture is maintained at 100° C. by the heating mantle. After reacting for about 16 hours, a sample of the reaction mixture was titrated for residual epoxide concentration. The residual epoxide was 0.134% w/w of oxirane oxygen. This is an epoxide conversion of 98%; the reaction was considered complete.

The reaction mixture was then purified by applying vacuum and distilling off excess water and acid left at the end of the reaction. Once the distillate flow ceases, the temperature of the reaction flask was slowly increased to about 235° C. When the temperature of the reaction flask reached 235° C., a sample was pulled and the acid number was 4.5 mg KOH/g. The reaction was continued at the same temperature for another 3 hours and 15 minutes and the acid number at that time was 1.0 mg KOH/g. The product was then cooled to 70° C. The resulting polyol had a hydroxyl number of 75 mg KOH/g, viscosity of 640 cP, moisture content of 0.02% w/w, and an acid number 0.9 mg KOH/g.

Example 5

Preparation of Polyurethane Foam Using a Polyol Derived from 100% Chicken Fat

Two 1.7 pcf foams were prepared using the hand-mix techniques described in Example 2. The control foam was prepared using a commercial soy-based polyol, Agrol® 2.0 (having a viscosity of 233 cPs, hydroxyl value of 70 mg KOH/g and an acid number of 0.4 mg KOH/g, available from Bio-Based Technologies LLC of Springdale, Ark.) and Arcol® F-3022, a petroleum based 3,000 molecular weight polyether triol, available from Bayer MaterialScience. The other foam was prepared using a renewable polyol of the invention (an hydroxylated pet food grade chicken fat (100%) from Tyson Foods, having a viscosity of 640 cP, hydroxyl value of 75 mg KOH/g and an acid number of 0.9 mg KOH/g) and Arcol® F-3022. The composition of the foam components in parts by weight are shown in the following table.

| Reaction Components | Control | Foam B |
|---|---|---|
| Arcol ® F-3022 | 85 | 85 |
| Agrol ® 2.0 | 15 | |
| 100% Chicken Fat Polyol | | 15 |
| Niax ® DP-1022 | 1.5 | 1.0 |
| Dabco ® 33LV | 0.04 | 0.04 |
| Niax ® A-1 | 0.04 | 0.04 |
| Niax ® L-595 | 0.7 | 0.7 |
| Water | 4.05 | 4.05 |

-continued

| Reaction Components | Control | Foam B |
|---|---|---|
| Dabco ® T-9 | 0.18 | 0.18 |
| Toluene Diisocyanate | 50.0 | 49.5 |

The components used in this example are described above in the previous example. The physical properties of the foams of Example 5 are shown in the following table.

| Property | Control | Foam B |
|---|---|---|
| Density (pcf) | 1.79 | 1.65 |
| Air Flow (cfm) | 5.5 | 4.7 |
| Ball Rebound (%) | 26 | 26 |
| Comp. Set ($C_t$-50%) | 3.96 | 5.24 |
| 25% IFD (lb/50 in$^2$) | 30.14 | 33.70 |
| 65% IFD (lb/50 in$^2$) | 56.72 | 59.71 |
| Support Factor | 1.9 | 1.8 |
| Tensile Str. (psi) | 15.98 | 16.07 |
| Elongation (%) | 317 | 269 |
| Tear Strength (N/mm) | 0.81 | 0.77 |
| Hysteresis (%) | 77.85 | 79.56 |

From the above examples it can be seen that the physical properties of the flexible foams produced using soybean oil polyol or foams based on either a mix of soybean oil and chicken fat or 100% chicken fat polyols have a very similar physical property profile.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any references to "or" herein is intended to encompass "and/or" unless otherwise stated.

While preferred embodiments of the present invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A process of preparing a hydroxy functional animal fat, the process comprising:
   (A) adding raw animal fat and optionally a vegetable oil, to an organic acid or peracid in a reactor to form mixture;
   (B) heating the mixture to about 50-150° C. with agitation generating a hot mixture;
   (C) adding 25 to 70% w/w of hydrogen peroxide/water to the hot mixture of (B) generating a reaction mixture;
   (D) heating the reaction mixture in a range of 50-150° C. for about 1 to 168 hours;
   (E) stripping off the bulk of the organic acid, water and other low boilers at or below a stripping temperature of 170° C. at a negative pressure that does not exceed 60 mmHg, until the reaction mixture tests for an acid number of about 10 mg KOH/g or less, creating the hydroxyl functional animal fat.

2. The process of claim 1, wherein step (E) comprises: wiped film evaporation, short path distillation, packed column stripping, or a combination thereof.

3. The process of claim 1, further comprising sparging the reaction mixture with a non-reactive gas during the stripping step (E).

4. The process of claim 3, wherein the non-reactive gas is steam or nitrogen.

5. The process of claim 1, wherein the organic acid is formic acid, acetic acid, propionic acid, lactic acid, performic acid, or peracetic acid.

6. The process of claim 1, wherein the animal fat is chicken fat, beef tallow, or lard.

7. The process of claim 6, wherein the animal fat is chicken fat.

8. The process of claim 1, wherein the vegetable oil is soybean oil.

9. The process of claim 1, wherein the reaction mixture tests for an acid number of about 4 mg KOH/g or less.

10. The process of claim 1, further comprising:
    (F) heating the hydroxy functional animal fat under vacuum to about 170-270° C. until the hydroxyl functional animal fat tests for an acid number of about 2 mg KOH/g or less.

11. A hydroxy functional animal fat having an acid number of about 6 mg KOH/g or less, and 0.1% w/w or less of water.

12. A hydroxy functional animal fat derived from one or more raw animal fat and one or more vegetable oils, having an acid number of about 6 mg KOH/g or less, and 0.1% w/w or less of water.

13. A process of preparing a hydroxy functional animal fat having an acid number of about 10 mg KOH/g or less, the process comprising contacting a raw animal fat and optionally a vegetable oil with hydrogen peroxide and an organic acid in the presence of water for a sufficient period of time, a sufficient temperature, and a sufficient pressure to form hydroxyl groups from unsaturated moieties in the raw animal fat, and thereafter separating any volatiles from the hydroxy functional animal fat by distillation, wherein the organic acid comprises formic acid, acetic acid, or propionic acid.

14. The process of claim 13, wherein the time of reaction is from 1 to 24 hours.

15. The process of claim 13, wherein the temperature ranges from about 50-135° C.

16. The process of claim 13, wherein the organic acid is a mixture of two organic acids.

17. The process of claim 13, wherein the distillation is carried out at or below 150° C.

18. The process of claim 13, wherein the distillation is wiped film evaporation, short path distillation, packed column stripping, or a combination of thereof.

19. The process of claim 13, wherein the hydroxy functional animal fat has an acid number of about 2 mg KOH/g or less.

20. The process of claim 13, wherein the distillation is carried out at a temperature of between about 175° C. and about 260° C.

21. A hydroxy functional animal fat prepared by the process of claim 1, wherein the hydroxyl functional animal fat is suitable for use in preparing polyurethanes.

22. A hydroxyl functional animal fat prepared by the process of claim 13, wherein the hydroxyl functional animal fat is suitable for use in preparing polyurethanes when prepared by the process of claim 13.

* * * * *

UNITED STATES PATENT AND TRADEMARK OFFICE
CERTIFICATE OF CORRECTION

PATENT NO.        : 9,234,159 B2
APPLICATION NO.   : 13/797692
DATED             : January 12, 2016
INVENTOR(S)       : Sorrell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 297 days.

Signed and Sealed this
Twenty-fourth Day of May, 2016

Michelle K. Lee
*Director of the United States Patent and Trademark Office*